(12) United States Patent
Lee et al.

(10) Patent No.: US 7,776,092 B2
(45) Date of Patent: Aug. 17, 2010

(54) ELASTOMERIC INTERVERTEBRAL DISC PROSTHESIS

(75) Inventors: Casey K. Lee, Florham Park, NJ (US); George Makris, West Orange, NJ (US); Alastair J. T. Clemow, Princeton, NJ (US)

(73) Assignee: Nexgen Spine, Inc., Whippany, NJ (US)

( * ) Notice: Subject to any disclaimer, the term of this patent is extended or adjusted under 35 U.S.C. 154(b) by 0 days.

(21) Appl. No.: 11/334,423

(22) Filed: Jan. 19, 2006

(65) Prior Publication Data

US 2007/0032874 A1    Feb. 8, 2007

Related U.S. Application Data

(60) Provisional application No. 60/644,527, filed on Jan. 19, 2005, provisional application No. 60/693,430, filed on Jun. 24, 2005.

(51) Int. Cl.
*A61F 2/44* (2006.01)
(52) U.S. Cl. .................. 623/17.15; 623/17.13
(58) Field of Classification Search ............ 606/61, 606/246–279; 623/17.11–17.16
See application file for complete search history.

(56) References Cited

U.S. PATENT DOCUMENTS

| | | | |
|---|---|---|---|
| 3,867,728 A | 2/1975 | Stubstad et al. | |
| 3,875,595 A | 4/1975 | Froning | |
| 4,349,921 A | 9/1982 | Kuntz | |
| 4,759,766 A | 7/1988 | Buttner-Janz | |
| 4,759,769 A | 7/1988 | Hedman | |
| 4,772,287 A | 9/1988 | Ray et al. | |
| 4,863,477 A | 9/1989 | Monson | |
| 4,904,260 A | 2/1990 | Ray et al. | |
| 4,911,718 A | 3/1990 | Lee et al. | |
| 4,932,969 A | 6/1990 | Frey et al. | |
| 4,946,378 A | 8/1990 | Hirayama et al. | |
| 5,047,055 A | 9/1991 | Bao et al. | |
| 5,071,437 A | 12/1991 | Steffee | |
| 5,123,926 A | 6/1992 | Pisharodi | |
| 5,171,281 A | 12/1992 | Parsons et al. | |
| 5,192,326 A | 3/1993 | Bao et al. | |
| 5,258,031 A * | 11/1993 | Salib et al. | ............... 623/17.15 |
| 5,306,308 A | 4/1994 | Gross et al. | |
| 5,306,309 A | 4/1994 | Wagner et al. | |
| 5,314,477 A | 5/1994 | Marnay | |
| 5,320,644 A | 6/1994 | Baumgartner | |

(Continued)

FOREIGN PATENT DOCUMENTS

EP    0 566 810 A1    10/1993

(Continued)

OTHER PUBLICATIONS

Szpalski, M., Spine arthroplasty: a historical review, Eur. Spine J. (2002), 11(Suppl.2): S65-S84.

(Continued)

*Primary Examiner*—Thomas C Barrett
*Assistant Examiner*—Andrew Yang
(74) *Attorney, Agent, or Firm*—Miles & Stockbridge P.C.

(57) ABSTRACT

In an intervertebral disc prostheses having a pair of rigid endplates and an elastomeric core structure between the endplates. The core structure is designed to provide desired functional characteristics of the prosthesis.

12 Claims, 7 Drawing Sheets

U.S. PATENT DOCUMENTS

| | | | |
|---|---|---|---|
| 5,370,697 | A | 12/1994 | Baumgartner |
| 5,401,269 | A | 3/1995 | Buttner-Janz |
| 5,458,642 | A | 10/1995 | Beer et al. |
| 5,514,180 | A | 5/1996 | Heggeness et al. |
| 5,534,028 | A | 7/1996 | Bao et al. |
| 5,534,030 | A | 7/1996 | Navarro et al. |
| 5,545,229 | A | 8/1996 | Parsons et al. |
| 5,556,431 | A | 9/1996 | Büttner-Janz |
| 5,562,738 | A | 10/1996 | Boyd et al. |
| 5,674,294 | A | 10/1997 | Bainville et al. |
| 5,674,296 | A | 10/1997 | Bryan et al. |
| 5,676,702 | A | 10/1997 | Ratron |
| 5,683,465 | A | 11/1997 | Shinne et al. |
| 5,824,093 | A | 10/1998 | Ray et al. |
| 5,824,094 | A | 10/1998 | Serhan et al. |
| 5,865,846 | A | 2/1999 | Bryan et al. |
| 5,888,226 | A | 3/1999 | Rogozinski |
| 5,893,889 | A | 4/1999 | Harrington |
| 5,976,186 | A | 11/1999 | Bao et al. |
| 6,113,637 | A | 9/2000 | Gill et al. |
| 6,136,031 | A | 10/2000 | Middleton |
| 6,139,579 | A | 10/2000 | Steffee et al. |
| 6,156,067 | A | 12/2000 | Bryan et al. |
| 6,162,252 | A | 12/2000 | Kuras et al. |
| 6,187,043 | B1 | 2/2001 | Ledergerber |
| 6,187,048 | B1 | 2/2001 | Milner et al. |
| 6,224,607 | B1 | 5/2001 | Michelson |
| 6,296,664 | B1 | 10/2001 | Middleton |
| 6,315,797 | B1 | 11/2001 | Middleton |
| 6,348,071 | B1 | 2/2002 | Steffee et al. |
| 6,368,350 | B1 | 4/2002 | Erickson et al. |
| 6,395,032 | B1 | 5/2002 | Gauchet |
| 6,419,704 | B1 | 7/2002 | Ferree |
| 6,419,706 | B1 | 7/2002 | Graf |
| 6,482,234 | B1 | 11/2002 | Weber et al. |
| 6,527,804 | B1 | 3/2003 | Gauchet et al. |
| 6,533,818 | B1 | 3/2003 | Weber et al. |
| 6,579,320 | B1 | 6/2003 | Gauchet et al. |
| 6,579,321 | B1 | 6/2003 | Gordon et al. |
| 6,582,466 | B1 | 6/2003 | Gauchet |
| 6,582,467 | B1 | 6/2003 | Teitelbaum et al. |
| 6,582,468 | B1 | 6/2003 | Gauchet |
| 6,592,624 | B1 | 7/2003 | Fraser et al. |
| 6,607,558 | B2 | 8/2003 | Kuras |
| 6,626,943 | B2 | 9/2003 | Eberlein et al. |
| 6,645,248 | B2 | 11/2003 | Casutt |
| 6,656,224 | B2 | 12/2003 | Middleton |
| 6,669,732 | B2 | 12/2003 | Serhan et al. |
| 6,682,562 | B2 * | 1/2004 | Viart et al. ............... 623/17.14 |
| 6,726,720 | B2 | 4/2004 | Ross et al. |
| 6,733,532 | B1 | 5/2004 | Gauchet |
| 6,740,118 | B2 | 5/2004 | Eiserman |
| 6,749,635 | B1 | 6/2004 | Bryan |
| 7,169,181 | B2 * | 1/2007 | Kuras ...................... 623/17.11 |
| 7,250,060 | B2 | 7/2007 | Trieu |
| 2001/0016773 | A1 | 8/2001 | Serhan et al. |
| 2001/0032017 | A1 | 10/2001 | Alfaro et al. |
| 2001/0051829 | A1 | 12/2001 | Middleton |
| 2002/0022888 | A1 | 2/2002 | Serhan et al. |
| 2002/0077701 | A1 | 6/2002 | Kuslich |
| 2003/0045939 | A1 | 3/2003 | Casutt |
| 2003/0074066 | A1 | 4/2003 | Errico et al. |
| 2003/0078667 | A1 * | 4/2003 | Manasas et al. .......... 623/17.15 |
| 2003/0100951 | A1 | 5/2003 | Serhan et al. |
| 2003/0135277 | A1 | 7/2003 | Bryan et al. |
| 2003/0208271 | A1 | 11/2003 | Kuras |
| 2004/0122517 | A1 | 6/2004 | Kuras et al. |
| 2004/0122518 | A1 | 6/2004 | Rhoda |
| 2004/0167626 | A1 | 8/2004 | Geremakis |
| 2004/0193273 | A1 | 9/2004 | Huang |
| 2004/0249462 | A1 | 12/2004 | Huang |
| 2004/0267367 | A1 | 12/2004 | O'Neil |
| 2005/0080487 | A1 * | 4/2005 | Schultz et al. ............ 623/17.13 |
| 2005/0131544 | A1 * | 6/2005 | Kuras et al. .............. 623/17.13 |
| 2005/0273111 | A1 | 12/2005 | Ferree |
| 2006/0079907 | A1 | 4/2006 | Boettiger et al. |
| 2006/0229724 | A1 | 10/2006 | Lechmann |
| 2006/0265075 | A1 * | 11/2006 | Baumgartner et al. .... 623/17.16 |
| 2006/0276900 | A1 * | 12/2006 | Carpenter ................ 623/17.15 |

FOREIGN PATENT DOCUMENTS

| | | |
|---|---|---|
| EP | 0 642 775 | 3/1995 |
| FR | 2 784 291 A1 | 4/2000 |
| WO | WO 89/03663 A1 | 5/1989 |
| WO | WO 90/11740 A1 | 10/1990 |
| WO | WO 95/19153 A1 | 7/1995 |
| WO | WO 99/22675 A1 | 5/1999 |
| WO | WO 03/090650 A1 | 11/2003 |
| WO | WO 2004/033516 | 4/2004 |
| WO | WO 2004/039291 A1 | 5/2004 |
| WO | WO 2005/072660 | 8/2005 |
| WO | WO 2005/007041 A1 | 12/2005 |

OTHER PUBLICATIONS

Hellier WG et al., Spine 1992, 127(6 Suppl.): Ss86-96.
Closkey RF et al., Spine 18(8): 1011-1015, 1993.
Hawkins MV et al., J. Orthop. Res. 12: 119-127, 1994.
McAfee, P. et al., Spine J. 4:48s, 2004.
Fraser RD et al., Spine J. 2004, 4(6S): 245s-251s.
Langrana NA, et al., Spine J 6, 267-278 (2006).

* cited by examiner

ELASTOMERIC INTERVERTEBRAL DISC PROSTHESIS

CROSS REFERENCE TO RELATED APPLICATION

This application claims the benefit of U.S. Provisional Application No. 60/644,527, filed Jan. 19, 2005, the entire disclosure of which is incorporated herein by reference, and the benefit of U.S. Provisional Application No. 60/693,430, filed Jun. 24, 2005, the entire disclosure of which is incorporated herein by reference.

BACKGROUND OF THE INVENTION

1. Field of the Invention

This invention relates to intervertebral disc prostheses and more particularly to intervertebral disc prostheses having rigid endplates and an elastomeric core.

2. Background Art

Low back pain is a very common pathological condition, affecting approximately 80% of the general population at some time. Although most of patients experience the painful symptoms only occasionally and recover fully, approximately 10% of these patients come to experience chronic and disabling low back pain in spite of various medical treatments.

The most common cause of chronic disabling low back pain is degeneration of one or more of the intervertebral discs that are positioned between the vertebrae of the spine and permit the various natural movements of the spinal column. Such degenerative disc disease (DDD) may become intractable to non-surgical treatment and have to be treated by surgical intervention. Spinal fusion has been a traditional and generally effective treatment method for chronic disabling low back pain that is not responding to non-operative treatments. More recently, alternative treatments involving replacement of the entire disc or its nucleus have been developed for treatment of discogenic pain.

The first generation of prostheses for replacement of degenerated intervertebral discs has generally incorporated mutually sliding surfaces of relatively hard materials to provide for the required intervertebral motion in flexion, extension, lateral bending and torsion. Although such prostheses have been found to be helpful, improvements in shock absorption and replication of the natural motion of the intact intervertebral disc have been sought.

Accordingly, subsequently developed prostheses have incorporated elastomeric members in order to provide for the required motion and shock absorption. Such prostheses typically include relatively hard endplates for contacting the endplates of adjacent vertebrae and fixing the prosthesis thereto, together with an elastomeric disc core, positioned between the hard endplates and fastened thereto.

However, in conventional designs of such intervertebral disc prostheses, the bone-contacting members, i.e., rigid endplates, typically have a and shape and size in a horizontal plane that conforms generally to the shape and size of the vertebral endplate; and the elastomeric element, positioned between the prosthesis endplates, also typically has a similar and shape and size. When such a prosthesis is subjected to stresses induced by bending of the spinal column, e.g., flexion, the elastomeric material at the periphery of the prosthesis may be compressed between the hard endplates and caused to bulge outwardly. Such deformation of the elastomeric component in repeated flexion may lead to eventual failure of the prosthesis. In some known prostheses, the outer periphery of the elastomeric core is provided with a concavity of the lateral wall to reduce the fixation stress in the peripheral region where the elastomer interfaces with the rigid, e.g., metal, endplates. However, even such a structure may be subject to eventual failure.

The present invention has been devised in view of the above background.

SUMMARY OF THE INVENTION

According to the invention, an intervertebral prosthesis is provided having generally rigid endplates for fixation to the upper and lower vertebrae of a spinal motion segment and an elastomeric core fastened between the endplates wherein at least an antero-posterior dimension of the interface between the core and at least one of the endplates is less than the antero-posterior dimension of the endplate. The lateral dimension of the interface between the core and at least one of the endplates may also be made smaller than the lateral dimension of the endplate.

Accordingly, it is an object of the invention to provide an intervertebral disc prosthesis having rigid endplates and an elastomeric core.

A further object is to provide such an intervertebral disc prosthesis wherein stress between the elastomeric core and the rigid endplates is reduced.

A further object is to provide an intervertebral disc prosthesis which is less prone to failure in use.

A further object is to provide an intervertebral disc prosthesis wherein the resistance to motions in flexion-extension, lateral bending, and torsion may be readily controlled.

According to one of its principal aspects, the present invention provides an intervertebral disc prosthesis for implanting between adjacent vertebrae in a spinal motion segment. The prosthesis comprises an upper rigid prosthesis endplate for fixation to an adjacent upper vertebra, and having a periphery, an antero-posterior dimension, and a transverse dimension; a lower rigid prosthesis endplate for fixation to an adjacent lower vertebra, and having a periphery, an antero-posterior dimension, and a transverse dimension; and an elastomeric core structure located between the prosthesis endplates and attached to the endplates. The elastomeric core structure includes at least one core member and has a total cross-sectional area in a horizontal plane and durometer hardness sufficient to provide sufficient compressive strength to support physiological axial loads.

According to one preferred feature, the elastomeric core structure has at least an average antero-posterior dimension, sufficiently less than at least one of the upper prosthesis endplate antero-posterior dimension and the lower prosthesis endplate antero-posterior dimension, such that the elastomer core does not protrude beyond the periphery of one of the prosthesis endplates during normal flexion and extension of the spinal motion segment.

According to another preferred feature, the core member has an antero-posterior dimension not greater than three times an axial height dimension of the core member.

According to yet another preferred feature, the core member has at least an average antero-posterior dimension not greater than three times an axial height dimension of said core member.

According to another preferred feature, the core member has a minimum antero-posterior dimension in a horizontal plane located axially between the endplates, the minimum antero-posterior dimension being not greater than three times an axial height dimension of the said core member.

According to still another of its principal aspects, the present invention provides an intervertebral disc prosthesis for implanting between adjacent vertebrae in a spinal motion segment, comprising an upper rigid prosthesis endplate for fixation to an adjacent upper vertebra, and having a periphery, an antero-posterior dimension, and a transverse dimension; a lower rigid prosthesis endplate for fixation to an adjacent lower vertebra, and having a periphery, an antero-posterior dimension, and a transverse dimension; and an elastomeric core structure located between the prosthesis endplates and attached to the endplates, the elastomeric core structure including a first elastomeric core member and a second elastomeric core member disposed outside an outer periphery of the first elastomeric core member, with the first elastomeric core member having durometer hardness greater than said second elastomeric core member.

Further objects, aspects, and advantages of the invention will be apparent from the description of the invention which follows.

DETAILED DESCRIPTION OF THE INVENTION AND PREFERRED EMBODIMENTS

The present invention provides an intervertebral prosthesis that utilizes flexible elastomeric materials confined between hard, typically metallic, endplate components in order to secure mechanical properties that can adequately substitute for the properties of a natural intervertebral disc. The intervertebral prosthesis of the invention is can be configured with adequate degrees of freedom to control the motion of a spinal motion segment in flexion-extension, lateral bending, and torsion when implanted to replace a damaged or degenerated spinal disc in a spinal column of a human patient. The invention will be explained and discussed in connection with the accompanying drawings.

Figure 1:
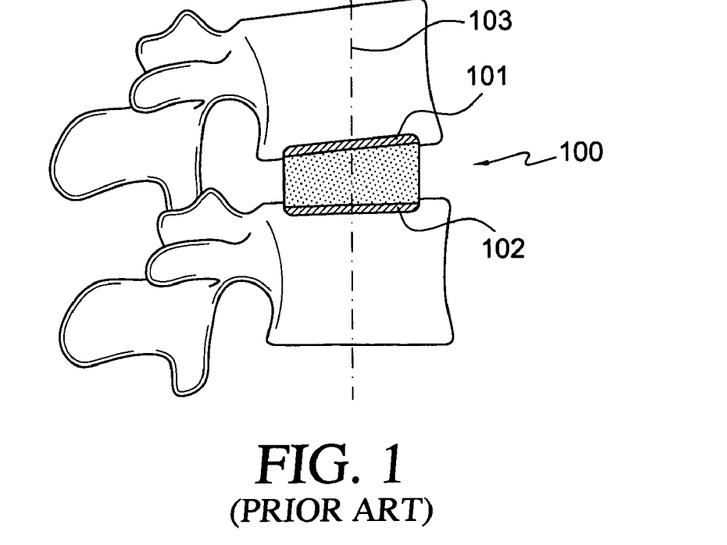
FIG. 1 is a schematic lateral view of an intervertebral disc of the prior art installed between adjacent vertebral bodies showing a median sagittal plane cross-sectional view of the prosthesis.
Figure 2:
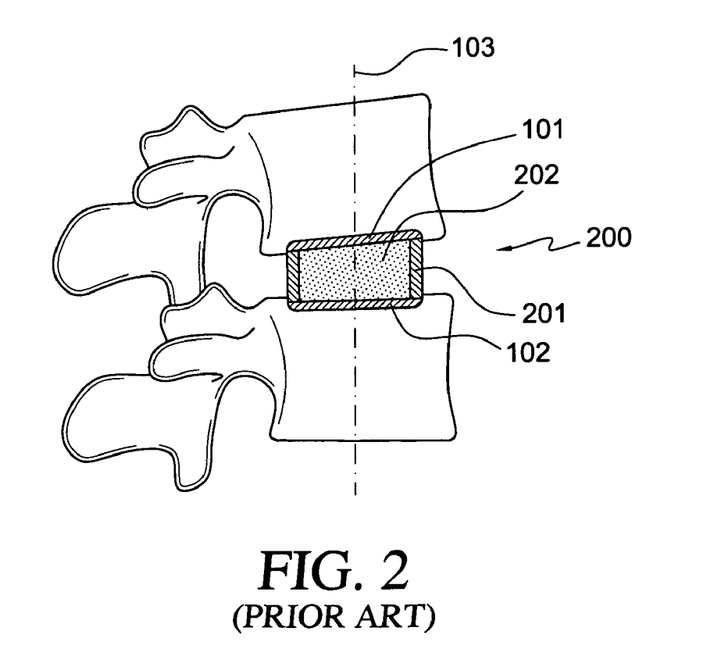
FIG. 2 is a schematic lateral view of another type of intervertebral disc of the prior art installed between adjacent vertebral bodies showing a median sagittal plane cross-sectional view of the prosthesis.

FIGS. 1 and 2 are partial sagittal sectional views of prior art illustrative examples wherein, as depicted in FIG. 1 the single elastomeric core 100 extends to the periphery of the hard endplates 101 and 102, and in FIG. 2 a multiple-durometer elastomeric core 200 is utilized, with the harder or reinforced elastomer 201 placed at the periphery of the softer elastomer 202. In both cases, the elastomer at the peripheral regions is highly compressed when the spinal motion segment is moved in flexion-extension and in lateral bending. Such prostheses, when exercised by such repeated compression, have been shown to exhibit failure due to both bulging and to impingement of the hard endplates 101 and 102 onto the bulging elastomer. Since the elastomeric core and hard endplate peripheries coincide, the centroids of area of the respective components in horizontal planes will coincide with a line 103.

Figure 3:
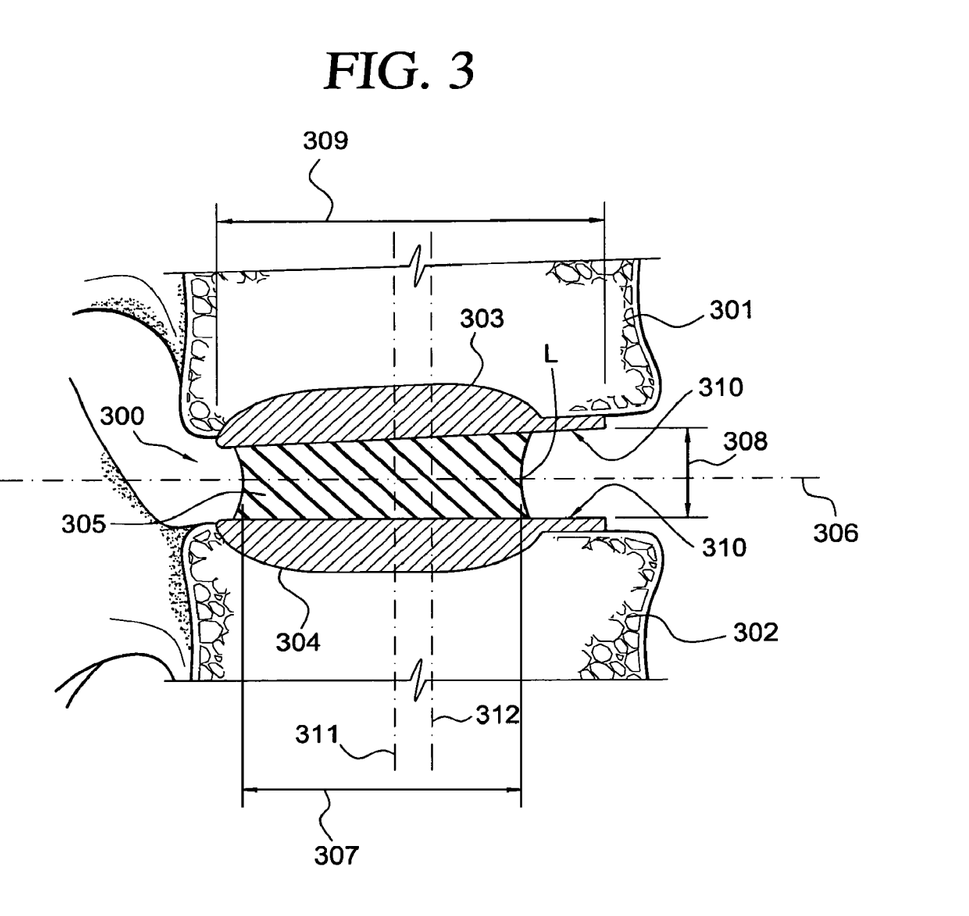
FIG. 3 is a sagittal sectional view of an embodiment of the invention.

FIG. 3 illustrates a typical configuration of the elements of a preferred embodiment of the invention. The preferred embodiment is illustrated as a sagittal plane (midline vertical plane) section with the elastomeric intervertebral disc prosthesis 300 implanted between adjacent vertebral bodies 301 and 302. The disc prosthesis 300 comprises a first or upper rigid plate 303, a second or lower rigid plate 304, and flexible elastomeric core 305 interposed between, and fixedly assembled to, the two rigid plates. For the disc prosthesis, the upper and lower rigid plates 303 and 304 are generally similar to each other, and the core 305 is symmetrically placed about the midline vertical plane. Rigid plates 303 and 304 are provided for fixation of the prosthesis to the vertebral bone and are made of biocompatible material, preferably a metallic material such as Ti6Al4V. Conventional metal fabrication methods may be used to fabricate the rigid plates. The elastomeric core 305 is preferably made of polyurethane and is fixedly connected to the rigid endplates by mechanical or adhesive means. Width 309 is the maximum sagittal width of endplates 303 and 304. Width 307 is the minimum width of elastomer 305 in the sagittal plane. Axial thickness 308 is the thickness of the elastomeric core 305 at the anterior limit L of width 307. Plane 306 is the horizontal plane for the section view of FIG. 4. As clearly illustrated, according to the invention, dimension 307 is significantly reduced relative to dimension 309, thereby providing for the endplate anterior margins 310 to converge in deep flexion without severe compression of the elastomeric core.

Figure 4:
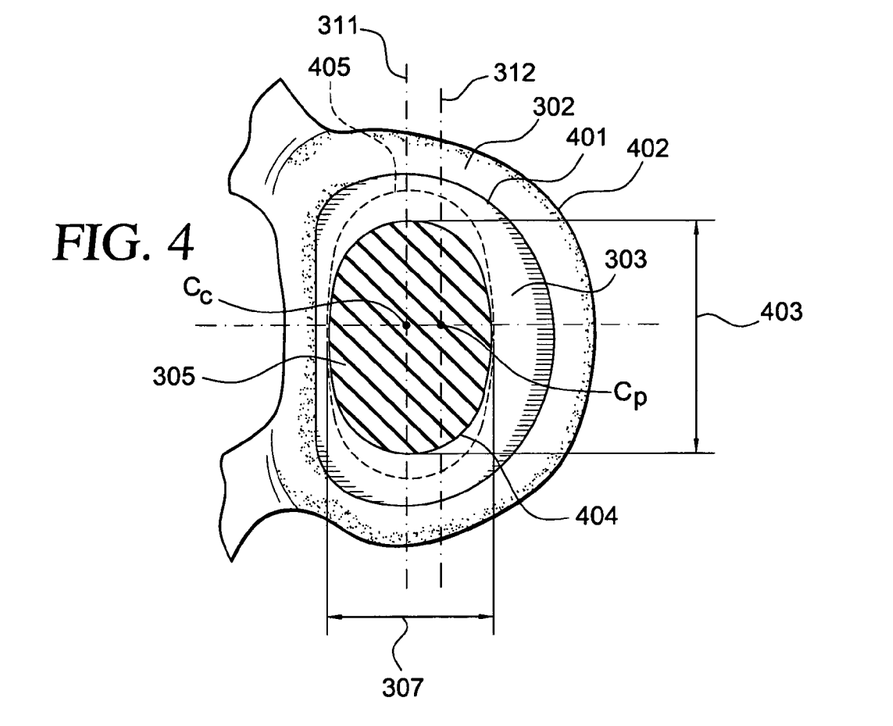
FIG. 4 is a horizontal section taken through a central plane within the elastomeric core of an embodiment of the invention.

FIG. 4 is a cross sectional view in the horizontal plane of disc prosthesis 300 at the level of plane 306 (containing the limit position L) of FIG. 3. The periphery 401 of endplate 303 is configured to be smaller but closely match the periphery 402 of the vertebral body endplate 302 since a large portion of the natural disc annulus is maintained during the surgical implantation of the disc prosthesis. Width 307 is the minimum width of elastomer 305 in the sagittal plane. Width 403 is the minimum width of elastomer 305 in the coronal plane. Lateral flexion stiffness of the normal lumbar disc is about double that of the anterior flexion, and it is desirable to maximize torsional stiffness. Thus, width 403 is advantageously equal or greater than 1.4 times width 307. Peripheral shape 404 of elastomer 305 is different from both peripheries 401 and 402. Shape 404 is a typical elastomeric shape for cervical disc applications where there are low torsional requirements for the proper functioning of the disc. Peripheral shape 405 is shown for purposes of comparison to shape 404 and depicts the elastomer shape of an alternate embodiment where higher torsional stiffness is desired, such as for the lumbar region.

In FIGS. 3 and 4, line 311 indicates a coronal plane containing the centroid $C_c$ of the cross-sectional area of core 305 in plane 306. Line 312 indicates a coronal plane containing the centroids $C_p$ (which are coincident in this example) of projected areas of the core contacting surfaces of endplates 303 and 304 onto plane 306. Such coronal planes shall be referred to hereinafter as centroidal planes. The posterior placement of centroid $C_c$ relative to projected centroids $C_p$ allows the disc flexion axis to be closer to the normal anatomical center of rotation.

FIGS. 5, 6, 7, 8 present sectional views similar to that of FIG. 4, providing illustrative examples of alternate embodiments. In these embodiments, the design parameters of FIG. 3 and FIG. 4 with respect to the endplates and general structure of the prosthesis are held constant while the alternate embodiments relate to the shape of elastomeric core 305.

Figure 5:
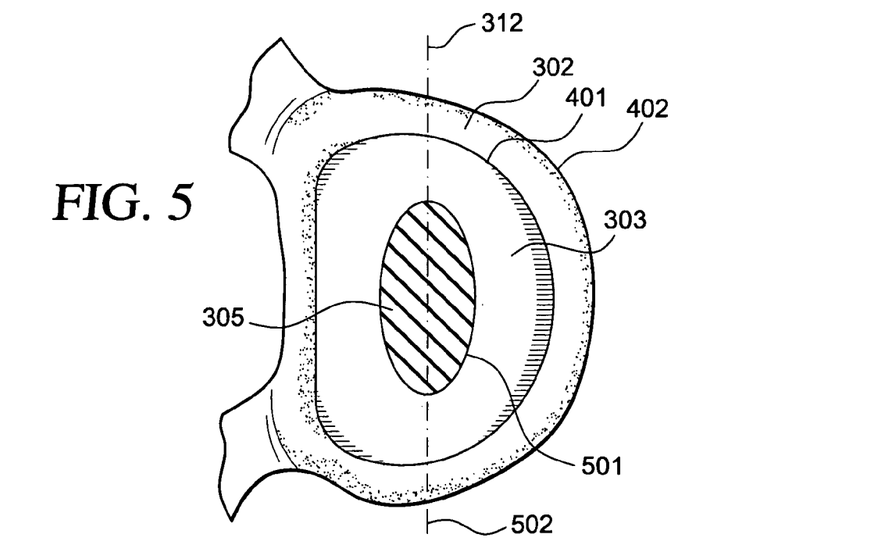
FIG. 5 is a horizontal section taken through a central plane within the elastomeric core of another embodiment of the invention, showing an elastomeric core having a generally elliptical cross-section.

FIG. 5 illustrates elastomeric core 305 having an elliptical shape 501 and positioned so as to have coinciding endplate and elastomer centroidal planes 312 and 502. The elliptical shape illustrated will provide low flexion stiffness.

Figure 6A:
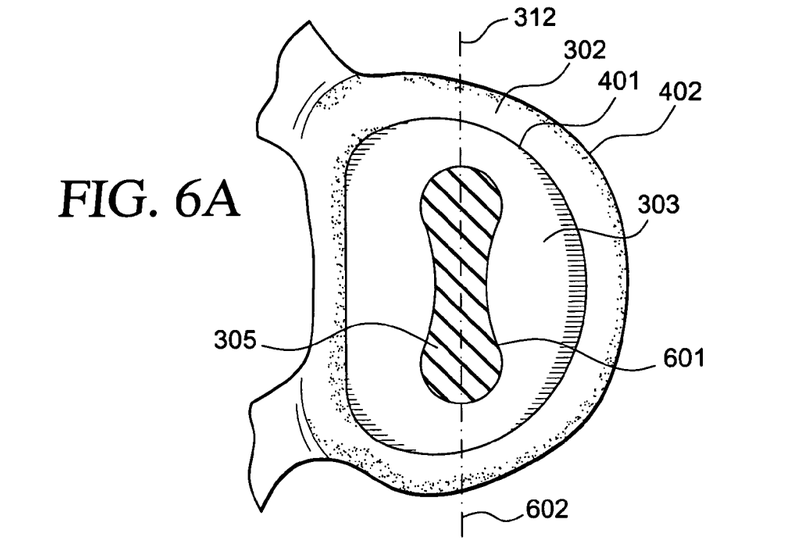
FIG. 6A is a horizontal section taken through a central plane within the elastomeric core of another embodiment of the invention, showing an elastomeric core having a generally peanut shell-shaped cross-section positioned generally centrally in an antero-posterior dimension of the prosthesis.

FIG. 6A illustrates elastomeric core 305 having peanut shell shape 601 and positioned so as to have coinciding endplate and elastomer centroidal planes 312 and 602.

Figure 6B:
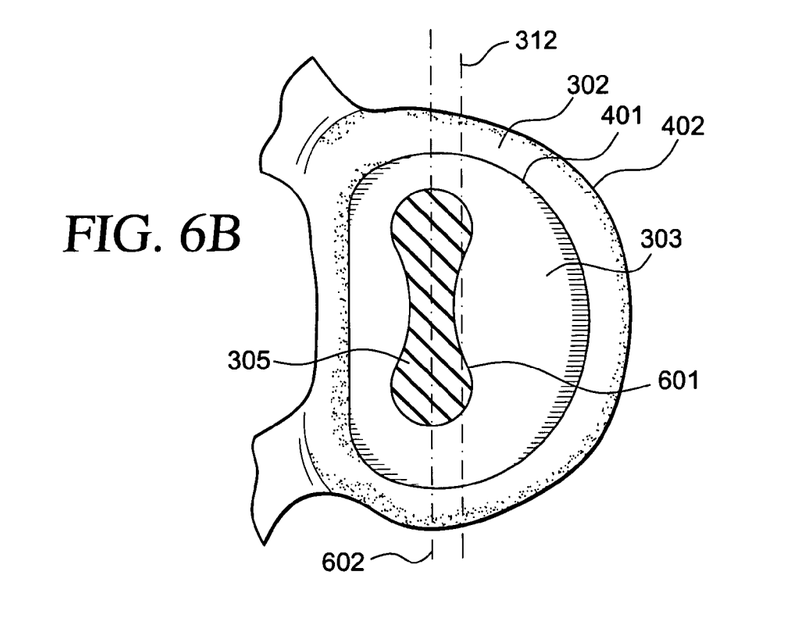
FIG. 6B is a horizontal section taken through a central plane within the elastomeric core of another embodiment of the invention, showing an elastomeric core having a generally peanut shell-shaped cross-section such as illustrated in FIG. 6A, positioned somewhat more posteriorly in an antero-posterior dimension of the prosthesis.

FIG. 6B illustrates elastomeric core 305 having peanut shell shape 601 and positioned so as to have elastomer centroidal plane 602 posterior to endplate centroidal plane 312. Flexion stiffness is similar to FIG. 6A, but with higher lateral and torsional stiffness.

Figure 7:
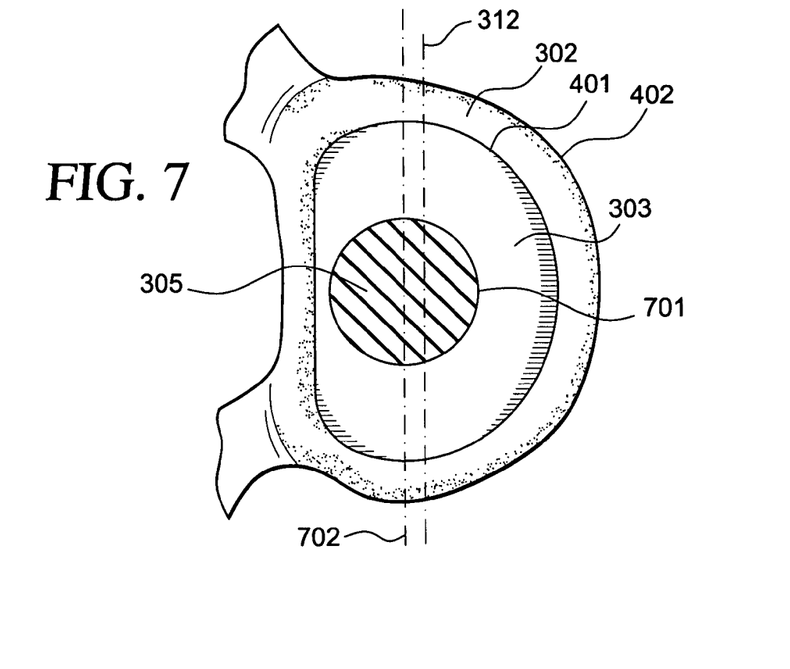
FIG. 7 is a horizontal section taken through a central plane within the elastomeric core of another embodiment of the invention, showing an elastomeric core having a generally circular cross-section.

FIG. 7 illustrates elastomeric core 305 having a circular shape 701 and positioned so as to have elastomer centroidal plane 702 positioned posterior to the endplate centroidal plane 312. In this embodiment, the prosthesis will exhibit low torsion and equal anterior and lateral flexion stiffness.

Figure 8:
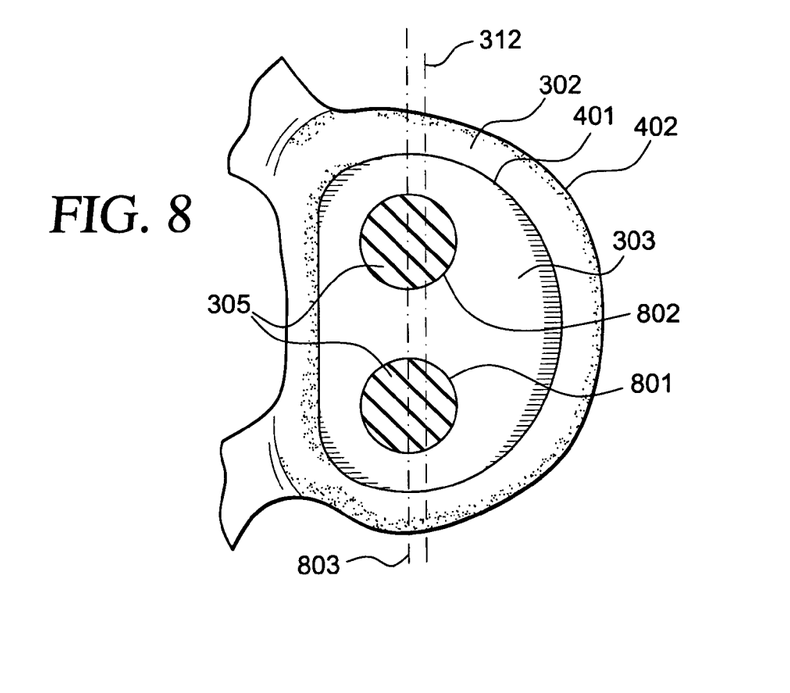
FIG. 8 is a horizontal section taken through a central plane within the elastomeric core of another embodiment of the invention, showing an elastomeric core comprising two elastomeric elements positioned laterally symmetrically with respect to a median sagittal plane.

FIG. 8 illustrates elastomeric core 305 having a two individual columns of circular shape 801 and 802 positioned so as to have elastomer centroidal plane 803 positioned posterior to the endplate centroidal plane 312. In this embodiment the prosthesis will exhibit high torsion and moderate lateral flexion stiffness.

Figure 9:
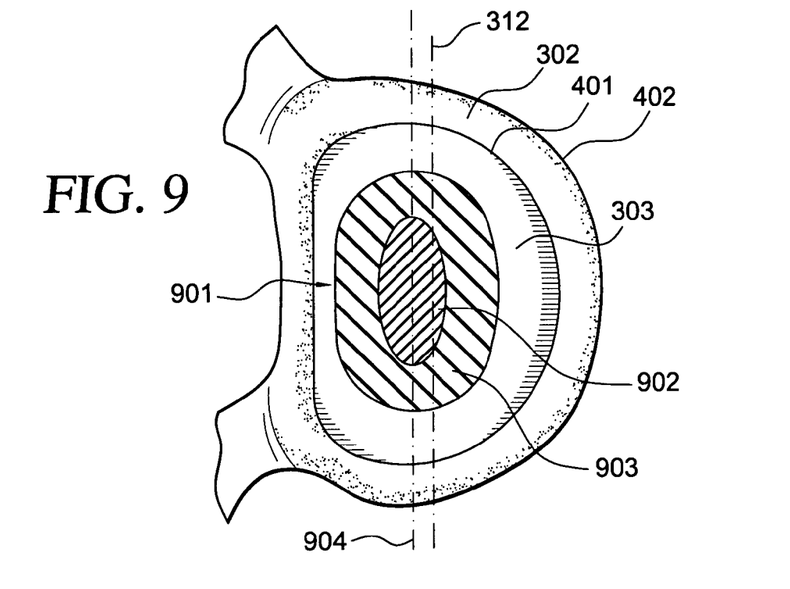
FIG. 9 is a horizontal section taken through a central plane within the elastomeric core of another embodiment of the invention, showing a central elastomeric element having a generally elliptical cross-section and having a relatively hard durometer surrounded by a peripheral elastomeric element having a somewhat softer durometer.
Figure 10:
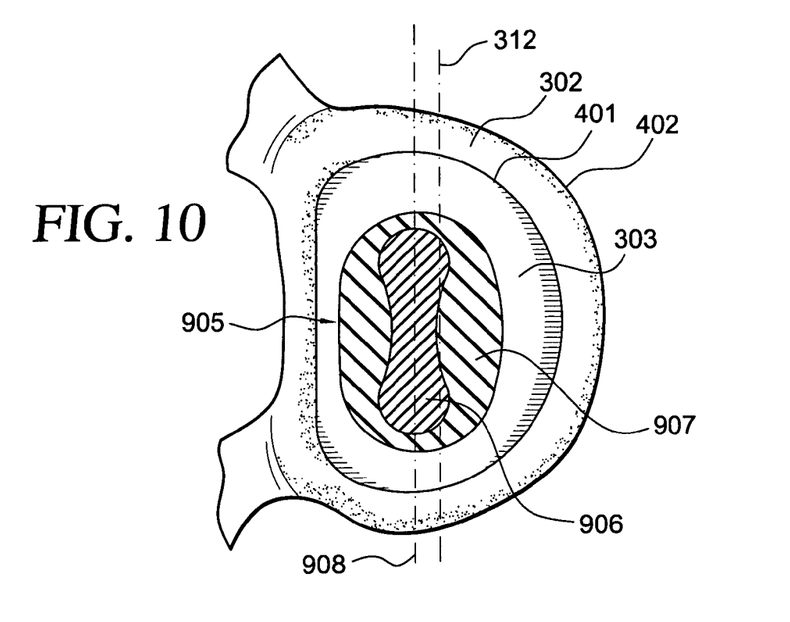
FIG. 10 is a horizontal section taken through a central plane within the elastomeric core of another embodiment of the invention, showing a central elastomeric element having a generally peanut shell-shaped cross-section and having a relatively hard durometer surrounded by a peripheral elastomeric element having a somewhat softer durometer.
Figure 11:
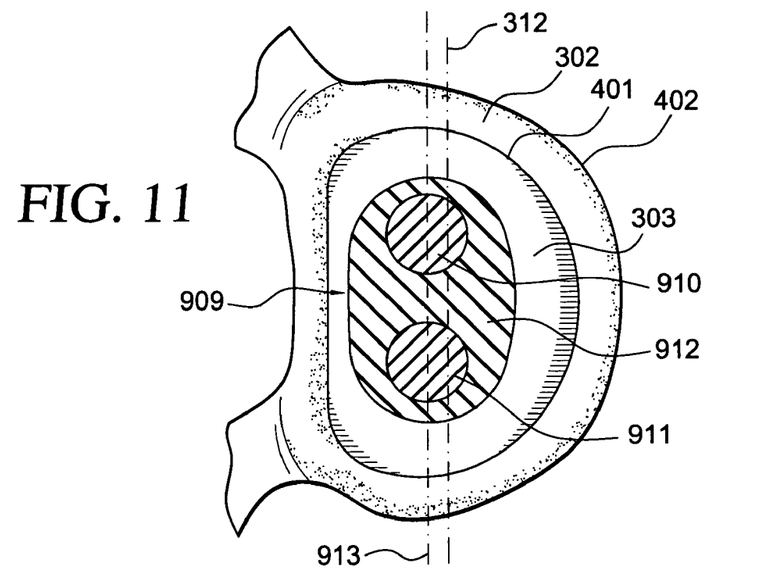
FIG. 11 is a horizontal section taken through a central plane within the elastomeric core of another embodiment of the invention, showing an elastomeric core comprising two elastomeric elements positioned laterally symmetrically with respect to a median sagittal plane and having a relatively hard durometer surrounded by a peripheral elastomeric element having a somewhat softer durometer.

FIGS. 9 to 11 refer to an alternate embodiment of the present invention wherein regions of the core element having different durometers are utilized to achieve desirable performance. Advantageously, lower durometer elastomer is used at the periphery of the elastomeric core where the largest deflections are experienced. For a higher durometer polymer, these larger deflections will result in higher stresses leading to a higher likelihood of debonding from the endplates. The higher durometer regions are introduced at regions of minimal deflection, normally relatively close to the anatomical center of motion. Higher durometer elastomers in such a central position provide for increased axial stiffness, and the peripheral lower durometer elastomers provide additional flexural stiffness allowing for the necessary deflections during normal disc range of motion.

FIGS. 9, 10, 11 show a view similar to that of FIG. 4 with illustrative examples of alternate embodiments. In these embodiments, the design parameters of FIG. 3 and FIG. 4 with respect to the endplates and general structure of the prosthesis are held constant, and the alternate embodiments relate to the shape and position of higher durometer regions within the elastomeric core 305 envelope.

FIG. 9 illustrates elastomeric core 901 having an elliptical shaped higher durometer region 902 and positioned internally of a lower durometer region 903 so as to have endplate centroidal plane 312 anterior to elastomer centroidal plane 904. Elastomer 902 provides additional axial and torsional stiffness with nominal contribution to additional flexion stiffness.

FIG. 10 illustrates elastomeric core 905 having a peanut-shell shaped higher durometer region 906 and positioned internally of a lower durometer region 907 so as to have endplate centroidal plane 312 and elastomer centroidal plane 908 somewhat posterior to the endplate centroidal plane. Elastomer 906 provides additional axial and lateral stiffness with respect to the example of FIG. 9 and with minimal contribution to additional flexion stiffness.

FIG. 11 illustrates elastomeric core 909 having a two individual columns constructed of higher durometer elastomer and having a circular shape 910 and 911 and positioned internally to the lower durometer region 912 having a combined elastomer centroidal plane 913 positioned posterior to the endplate centroidal plane 312. In an alternate embodiment, the regions 910 and 911 are constructed from lower durometer elastomer and region 912 from a higher durometer elastomer.

Figure 12:
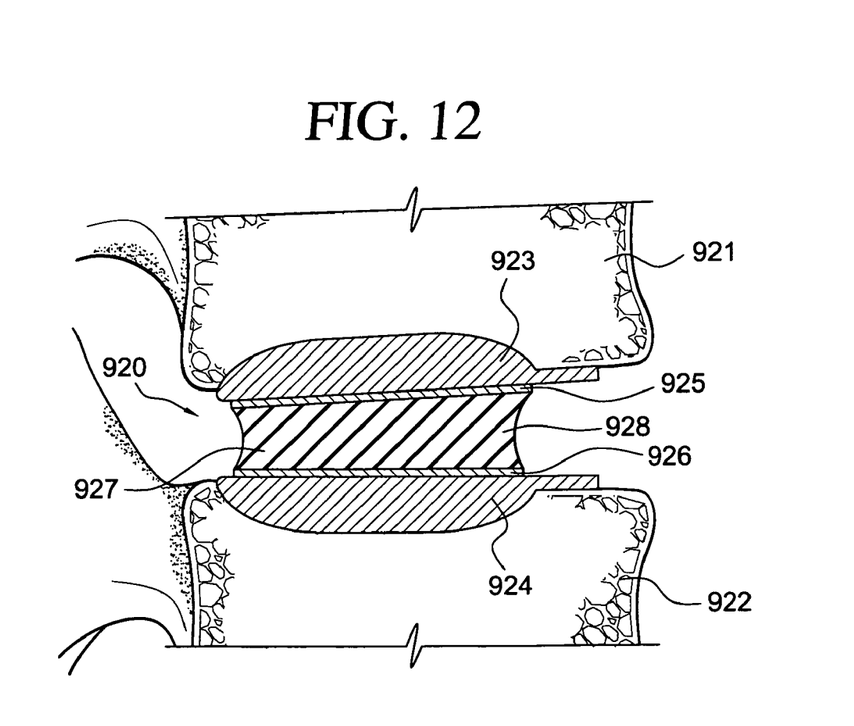
FIG. 12 is a median sagittal plane cross-sectional view of a prosthesis of the invention implanted between two vertebrae of a spinal motion segment.

FIG. 12 shows a variation of the preferred embodiment of FIG. 4. It is illustrated in a sagittal plane section with the elastomeric intervertebral disc prosthesis 920 implanted between adjacent vertebral bodies 921 and 922. The disc prosthesis 920 comprises a first or upper rigid plate 923, a second or lower rigid plate 924, intermediate elastomeric plates 925 and 926 fixedly assembled to the rigid plates 923 and 924, and a flexible elastomeric core 927 interposed between and fixedly assembled to the two intermediate plates 925 and 926. The intermediate plates provide for stress reduction transition between the very low modulus flexible elastomeric core and the extremely stiff hard endplates. Additionally, the transition plates provide for higher mechanical fixation strength to the typically metallic hard endplates as well as a stronger elastomer-to-elastomer adhesive bond to the elastomeric core side. The peripheral wall 928 of elastomeric core 927 advantageously forms a concavity so as to provide for additional fixation area to intermediate plates 925 and 926.

EXAMPLE

This example illustrates the determination of a preferred ratio of anterior-posterior dimension to core height.

A series of experiments was conducted on a polycarbonate polyurethane disc of constant durometer (80 A). The ratio of the anterior-posterior width of the core to its height was varied, and the behavior of the disc as it was made to flex repeatedly to 10 degrees was examined. The results are shown below in Table 1.

TABLE 1

| | Ratio of anterior-posterior dimension to core height | | | |
|---|---|---|---|---|
| | 1:1 | 2:1 | 3:1 | 4:1 |
| Effect of 10° flexion | Buckled inwards | Neutral | Slight bulging | Bulging and impingement of polymer on endplate |

Test Conditions:
  Elastomer hardness: 80 A durometer
  Disc height: 5 mm for all samples
  Anterior-posterior dimension varied to produce varied ratio of core height to anterior-posterior (AP) dimension The results suggest that a ratio of 3:1 (anterior-posterior dimension to core height) or less is required to ensure that impingement of the core on the endplates does not occur. Thus, on the basis of this data, a ratio of 2:1 would appear ideal to eliminate bulging and the danger of polymer impingement. However, the mechanical properties of elastomers, coupled with the desire to match the flexural stiffness of a natural disc, dictates maximizing the shape area of the device. Since the intervertebral height is a design envelope limiting factor in practice, for a given height 308, width 307 has a proportionally maximum value of three times height 308. For ratios of higher than three, impingement and bulging become detrimental to device integrity.

The invention having been described above in terms of certain embodiments, it will be apparent to those skilled in that that many changes and alterations can be made without departing from the spirit and principles of the invention.

We claim:

1. An intervertebral disc prosthesis for implanting between adjacent vertebrae in a spinal motion segment, comprising:
   an upper rigid prosthesis endplate for fixation to an adjacent upper vertebra, and having a periphery, an antero-posterior dimension, and a transverse dimension,
   a lower rigid prosthesis endplate for fixation to an adjacent lower vertebra, and having a periphery, an antero-posterior dimension, and a transverse dimension, and
   an elastomeric core located between said prosthesis endplates and attached to said endplates,
   said elastomeric core including at least a first elastomeric core member and having a total cross-sectional area in a horizontal plane and durometer hardness sufficient to provide sufficient compressive strength to support physiological axial loads, and
   said elastomeric core having at least an average antero-posterior dimension, sufficiently less than at least one of said upper prosthesis endplate antero-posterior dimension and said lower prosthesis endplate antero-posterior dimension, such that said elastomeric core does not protrude beyond the periphery of one of said prosthesis endplates during normal flexion and extension of said spinal motion segment,
   wherein a maximum antero-posterior dimension of said elastomeric core in a central horizontal plane of said prosthesis is less than a maximum transverse dimension of said elastomeric core in said central horizontal plane and each prosthesis endplate has a ratio of a maximum antero-posterior dimension thereof to a maximum transverse dimension thereof that is different from a ratio of said maximum antero-posterior dimension of said elastomeric core to said maximum transverse dimension of said elastomeric core in said central horizontal plane.

2. The intervertebral prosthesis of claim 1, wherein said maximum transverse dimension of said elastomeric core in said central horizontal plane is not less than 1.4 times said maximum anteroposterior dimension of said elastomeric core in said central horizontal plane.

3. The intervertebral disc prosthesis of claim 1, wherein said elastomeric core has a centroid positioned posterior to a centroid of at least one of said upper prosthesis endplate and said lower prosthesis endplate.

4. An intervertebral disc prosthesis for implanting between adjacent vertebrae in a spinal motion segment, comprising:
   an upper rigid prosthesis endplate for fixation to an adjacent upper vertebra,
   a lower rigid prosthesis endplate for fixation to an adjacent lower vertebra, and
   an elastomeric core structure located between said prosthesis endplates and attached to said endplates,
   said elastomeric core structure including at least one elastomeric core member fixedly attached to said endplates and having a total cross-sectional area in a horizontal plane and durometer hardness sufficient to provide sufficient compressive strength to support physiological axial loads,
   wherein said elastomeric core member includes only one elastomer and is a unitary body devoid of any axial through-hole, having a generally concave periphery and a height in a midline vertical plane of said core member that is non-decreasing in a posterior to anterior direction essentially entirely over a maximum antero-posterior dimension of said core member,
   wherein said antero-posterior dimension in said midline vertical plane is not greater than about three times an axial height dimension of said core member, and
   wherein a maximum anteroposterior dimension of said unitary elastomeric body in a central horizontal plane of said prosthesis is less than a maximum transverse dimension of said unitary elastomeric body in said central horizontal plane, and each prosthesis endplate has a ratio of a maximum antero-posterior dimension thereof to a maximum transverse dimension thereof that is different from a ratio of said maximum antero-posterior dimension of said unitary elastomeric body to said maximum transverse dimension of said unitary elastomeric body in said central horizontal plane.

5. The intervertebral disc prosthesis of claim 4, wherein said antero-posterior dimension is a minimum antero-posterior dimension in said midline vertical plane.

6. The intervertebral disc prosthesis of claim 4, wherein said unitary elastomeric body has a centroid positioned posterior to a centroid of at least one of said upper prosthesis endplate and said lower prosthesis endplate.

7. The intervertebral prosthesis of claim 4, wherein said maximum transverse dimension of said unitary elastomeric body in said central horizontal plane is not less than 1.4 times said maximum anteroposterior dimension of said unitary elastomeric body in said central horizontal plane.

8. The intervertebral disc prosthesis of claim 7, wherein said unitary elastomeric body has a centroid positioned posterior to a centroid of at least one of said upper prosthesis endplate and said lower prosthesis endplate.

9. The intervertebral disc prosthesis of claim 4, wherein said antero-posterior dimension in said midline vertical plane is about two times of the axial height dimension of said core member.

10. An intervertebral disc prosthesis for implanting between adjacent vertebrae in a spinal motion segment, comprising:

an upper rigid prosthesis endplate for fixation to an adjacent upper vertebra, and a lower rigid prosthesis endplate for fixation to an adjacent lower vertebra, wherein said upper and lower endplates are coupled through a single unitary elastomeric body, devoid of any axial through-hole, which is fixedly attached to said upper and lower endplates, said unitary elastomeric body having a generally concave periphery, a maximum antero-posterior dimension in a midline vertical plane of said prosthesis that is less than a respective maximum antero-posterior dimension of each of said upper and lower prosthesis endplates in said midline vertical plane, and a height in said midline vertical plane that is non-decreasing in a posterior to anterior direction essentially entirely over said maximum antero-posterior dimension of said elastomeric body, wherein, in said midline vertical plane, said unitary elastomeric body has an antero-posterior dimension not greater than about three times an axial height dimension thereof, and wherein said maximum antero-posterior dimension of said unitary elastomeric body in a central horizontal plane of said prosthesis is less than a maximum transverse dimension of said unitary elastomeric body in said central horizontal plane, and each prosthesis endplate has a ratio of said maximum antero-posterior dimension thereof to a maximum transverse dimension thereof that is different from a ratio of said maximum antero-posterior dimension of said unitary elastomeric body to said maximum transverse dimension of said unitary elastomeric body in said central horizontal plane.

11. The intervertebral disc prosthesis of claim 10, wherein said unitary elastomeric body has a centroid positioned posterior to a centroid of at least one of said upper prosthesis endplate and said lower prosthesis endplate.

12. The intervertebral disc prosthesis of claim 10, wherein, in said midline vertical plane, said unitary elastomeric body has an antero-posterior dimension about two times of the axial height dimension.

\* \* \* \* \*